United States Patent [19]

Mikkelsen

[11] Plant 4,202

[45] Jan. 31, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,023

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel impatiens variety having deep orange-red blossoms borne profusely on a semi-compact plant.

1 Drawing Figure

1

The present invention relates to a new and distinctive cultivar of Impatiens plant, botanically known as Impatiens and known by the cultivar name Lafayette. The new cultivar was developed by me through controlled breeding by crossing the unpatented cultivar No. 349,583, a variety of the U.S. Department of Agriculture (seed parent) with an unknown seedling of the inventor (pollen parent). Asexual reproduction of terminal or stem cuttings by me in Ashtabula, Ohio has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Semi-compact growth habit that breaks well after the removal of the apical tip.
2. Internodal spacing of 2" to 3" gives excellent exposure of foliage and flowers.
3. Sharp, narrow, central leaf variegation is distinctive against dark green outer leaf edges.
4. Variegation develops quite quickly on the foliage so that new side shoots used in propagation are usually bi-colored.
5. Flower color is deep orange-red with some development of a light colored throat.
6. Flowering is profuse.
7. The spur is nearly the same color as the petals and has a sharp curve beginning at its base.
8. The top petal is separated from the other four with its apice nearly pointed. The two side petals are smaller than other three, and the two bottom petals are largest with their apice recessed at vein. Flowers are 5 cm. in diameter.
9. A semi-compact, medium height, upright, well branching herb.

The accompanying colored photograph illustrates the overall appearance of the new cultivar and shows the colors as true as it is reasonably possible to obtain in a colored reproduction of this type.

The following is a detailed description of my new Impatiens cultivar based on plants produced under commercial practices at the greenhouses of Mikkelsens Inc., Ashtabula, Ohio. Color references are made to the Royal Horticultural Society Colour Chart except where general terms of ordinary dictionary significance are used.

2

Parentage: A controlled pollination of U.S. Department of Agriculture plant acquisition No. 349,583 crossed with an unknown Mikkelsen seedling.

Propagation:

*Type cutting.*—Top cuttings 2–3 cm. long.

*Time to visible rooting.*—10 days at 21° C summer, 15 days at 20° C winter.

*Rooting habit.*—Typical for Impatiens, rapid, dendritic and very profuse in primary and secondary roots.

Plant description:

*Form.*—A semi-compact, medium height, upright, well branching herb.

*Habit of growth.*—Medium to fast, strong upright growth with excellent branching habits.

*Foliage.*—Varies from soft lush appearance in very young plants to well textured leathery leaf on mature flowering plants, with distinct yellow variegation. Size: Can vary from 5 cm. up to 6 cm. wide by 10 cm. to 15 cm. long; petioles generally 2 cm. long but up to 5 cm. on soft succulent growth. Shape: Nearly perfectly elliptical, apex acuminate, base acute but tending to cuneate. Texture: Highly glabrous, generally rugose. Margin: Entire, minutely ciliolate. Color: Young soft foliage, top side green 137A, yellow central variegation, under side near green 138B; Mature foliage, top side darker than yellow green 147A with enlarged yellow variegation, yellow orange 16B, under side near green 137D. Venation: Pinnately, tending to arcuate.

Flowering description:

*Flowering habits.*—Flowering occurs at the nodes of semi-mature to mature plants usually one flower per leaf or less, unusual to have more than one per leaf. The attractiveness of the plant is enhanced by several flowers being in bloom at the same time at the same node, and flowering occurs at several nodes at the same time.

*Natural flowering season.*—Flowering is considered indeterminate and occurs all year.

*Flower buds.*—Symmetrically conical covered with three sepals. A red to orange hollow spur 5 cm. long emerges from the bottom sepal. A sepal like scale at the midrib on the back of the top petal is evident.

*Flowers borne.*—Single flowers borne on a pink to colorless pedicel 6–7 cm. long by 1.5 mm. to 2 mm. in diameter.

*Quantity of flowers.*—Typical for most New Guinea hybrids but the high number in flower at any one time is unique.

*Petals.*—Shape: Top petal nearly circular, two small side petals egg shape and two larger lower petals tending to heart shape, edges irregular. Color: top side in winter when opening luminescent bright orange red, more lively than 33A or 40B, fading to 33B to 32A; flower throat light pink; under side near 41C. Number of petals: 5. Size of petals: 2 cm. to 2.5 cm. in diameter, flower is 4.5 to 5 cm. in diameter.

*Reproductive organs.*—Stamens: One in number. Anther shape: Hooded over pistil, creamy white in color. Pollen color: Cream to white. Pistils: Stigma shape: Circular, flat, irregular surface, green in color. Style: Green in color. Ovaries:

One in number, size immature to 5 mm., dark green in color.

I claim: a

1. A new and distinct cultivar of Impatiens known by the cultivar name Lafayette and particularly characterized as to uniqueness by the combined characteristics of semi-compact growth habit that breaks well after the removal of the apical tip; internode spacing which provides excellent exposure to foliage and flowers; sharp, narrow leaf variegation, with the variegation developing quickly; deep orange-red flower color and profuse flowering; a spur which is curved and the same color as the flower petals, and its five flower petals, the top one of which is separated from the other four with its apex nearly pointed, and the bottom two of which are largest in diameter and have their apices recessed at the vein.

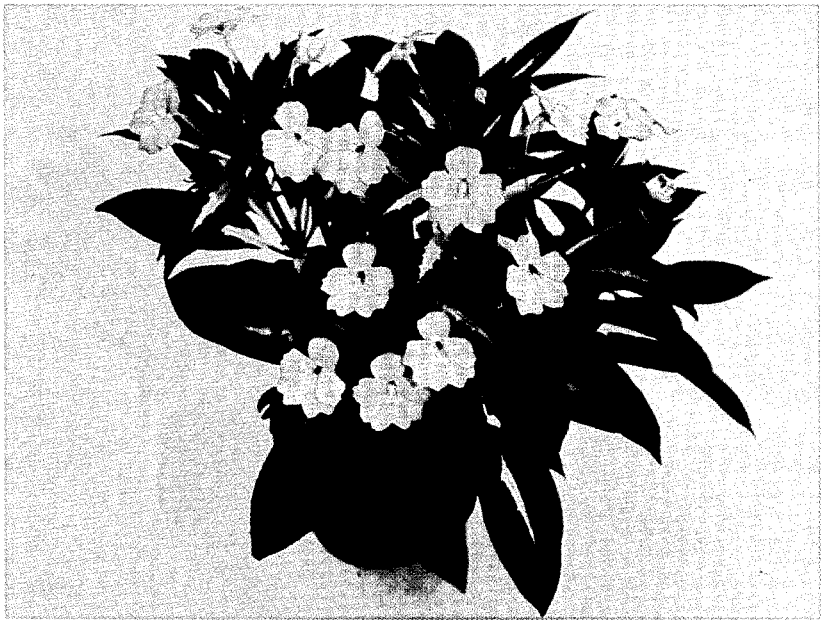

* * * * *